United States Patent [19]
Morris et al.

[11] Patent Number: 6,103,081
[45] Date of Patent: Aug. 15, 2000

[54] HEAT SINK FOR CAPILLARY ELECTROPHORESIS

[75] Inventors: Michael D. Morris; Tracey L. Rapp, both of Ann Arbor, Mich.

[73] Assignee: The Regents of The University of Michigan, Ann Arbor, Mich.

[21] Appl. No.: 08/763,908

[22] Filed: Dec. 11, 1996

[51] Int. Cl.⁷ .................................................. G01N 27/26
[52] U.S. Cl. ........................................... 204/451; 204/601
[58] Field of Search ...................................... 204/451, 601

[56] References Cited

U.S. PATENT DOCUMENTS

| | | | |
|---|---|---|---|
| 3,620,958 | 11/1971 | Dijksterhuls et al. | 204/508 |
| 4,898,658 | 2/1990 | Karger et al. | 204/603 |
| 5,021,646 | 6/1991 | Weinberger et al. | 250/227.11 |
| 5,085,757 | 2/1992 | Karger et al. | 204/299 R |
| 5,122,253 | 6/1992 | Christianson | 204/299 R |
| 5,164,064 | 11/1992 | Dill et al. | 204/299 R |
| 5,183,101 | 2/1993 | Penaluna et al. | 165/47 |
| 5,198,091 | 3/1993 | Burolla et al. | 204/299 R |
| 5,385,654 | 1/1995 | Kelly et al. | 204/180.1 |
| 5,402,160 | 3/1995 | Kadowaki et al. | 347/18 |
| 5,685,965 | 11/1997 | Allington | 204/451 |
| 5,691,013 | 11/1997 | Soufiane et al. | 428/34.4 |
| 5,730,850 | 3/1998 | Kambara et al. | 204/603 |

FOREIGN PATENT DOCUMENTS 03172756  7/1991  Japan .

OTHER PUBLICATIONS

Nelson et al. ("Use of Peltier Thermoelectric Devices to Control Column Temperature in High–Performance Capillary Electrophoresis," J. Chromat., 480(Month Unknown1989), 111–127).

English language translation of Kobayashi et al. (JP 03172756), Jul., 1991.

JAPIO abstract of Shoichi et al. (JP 03172756 A), Jul. 26, 1991.

A. Guttman et al., "Effect of Temperature On the Separation of DNA Restriction Fragments In Capillary Gel Electrophoresis," *J. Chromatogr.*, 559:285–294 (1991) Month Unknown.

S.L. Petersen et al., "Effects of Capillary Temperature Control and Electrophoretic Heterogeneity on Parameters Characterizing Separations of Particles By Capillary Zone Electrophoresis," *Anal. Chem.*, 64:1676–1681 (1992) Month Unknown.

J.H. Knox, "Thermal Effects and Band Spreading in Capillary Electro–Separation," *Chromatographia*, 26:329–337 (1988) Month Unknown.

K.D. Davis et al., "Spatially Resolved Temperature Measurements in Electrophoresis Capillaries by Raman Thermometry," *Anal. Chem.*, 65:293–298 (1993) Month Unknown.

K.L. Liu et al., "Raman Spectroscopic Measurement of Spatial and Temporal Temperature Gradients in Operating Electrophoresis Capillaries," *Anal. Chem.*, 66:3744–3750 (1994) Month Unknown.

Flexible Fused Silica Capillary Tubing Standard Product List, Polymicro Technologies, Inc., Phoenix, AZ, (1996) Month Unknown.

F.W. Peek et al., Dielectric Phenomena in High Voltage Engineering, Second Edition (pp. 4, 8–37); McGraw–Hill Book Co., Inc.: New York, NY (1920) Month Unknown.

T.L. Rapp, "Temperature Control in Capillary Electrophoresis," Thesis, University of Michigan, Ann Arbor, Michigan, 1996, Appendix.

J.P. Holman, Heat Transfer, Sixth Edition; McGraw–Hill Book Company, 43–55 (1986) Month Unknown.

Technical data Code 9658, *Physical Properties of MACOR*, Corning Glass Works Month Unknown Year Unknown.

*Primary Examiner*—Jill Warden
*Assistant Examiner*—Alex Noguerola
*Attorney, Agent, or Firm*—Medlen & Carroll, LLP

[57] ABSTRACT

A cooling means for a capillary electrophoresis system is described. The cooling means is designed for efficient heat dissipation and operates without arcing at voltages higher than 30 kV.

12 Claims, 7 Drawing Sheets

HEAT SINK FOR CAPILLARY ELECTROPHORESIS

"This invention was made with government support under Cooperative Agreement GM37006 awarded by the Department of Commerce, National Institute of Standards and Technology, Advanced Technology Program. The Government has certain rights in the invention."

FIELD OF THE INVENTION

The invention relates to the field of electrophoresis and more particularly, to means for cooling capillary electrophoresis devices.

BACKGROUND

Capillary electrophoresis (CE) is a chemistry separation technique which utilizes the differences in solute electrophoretic velocity to isolate the various components of a sample. Electro-osmotic flow is the bulk flow of buffer from a first buffer reservoir to a second buffer reservoir through the capillary due to the shearing movement of a diffuse layer of cations past a more firmly held, dense layer, interacting with integral, anionic groups of the capillary wall.

Factors which influence the velocity of electro-osmotic flow are: electrical field strength; buffer dielectric constant; zeta potential (the electrical potential existing between diffuse and compact cationic layers); and buffer viscosity (which is dependent on bulk properties of the buffer and the temperature of the buffer).

Electrophoretic force is the force applied to charged particles residing in an electrical field, and neutral or uncharged molecules are not affected. Positively charged molecules (cations) migrate towards the cathode while negatively charged molecules (anions) move towards the anode. Factors controlling solute electrophoretic velocity are: molecular charge; electrical field strength; viscosity of the migration media; and solute molecular geometric factors.

The net velocity at which a solute travels in an uncoated, open capillary tube during CE is the vector sum of the electro-osmotic and electrophoretic velocities. Buffer viscosity plays a significant role for both of these phenomenon. Both electrophoretic and electro-osmotic velocities are inversely proportional to buffer viscosity, thus affecting the net migration velocity for all solutes. When an electrical field is applied to a capillary which contains buffer, joule heating occurs.

Joule heating is a major problem in capillary electrophoresis (CE). At one extreme, the solution can be heated to boiling, putting an end to the separation. Even at temperatures below boiling, elevated internal temperature increases diffusional spreading and Taylor dispersion. (See A. Guttman el al., *J. Chromatogr.*, 559:285–294 (1991); S. L. Petersen el al., *Anal. Chem.*, 64:1676–1681 (1992); J. H. Knox, *Chromalographia*, 26:329–337 (1988).)

Some analytes, such as proteins, are themselves heat sensitive, and undergo irreversible changes at temperatures well below the boiling point of water. For such reasons, CE is usually performed in low ionic strength buffers or at moderate voltages (10–25 kV), or both.

Although heat dissipation from a capillary can be efficient, often it is not perfect. In typical buffers, temperature elevation in capillaries is readily observable at normal (100–350 V/cm) operating electric fields. (See K. D. Davis el al.,*Anal. Chem.*, 65:293–298 (993); K. L. Liu et al.,*Anal. Chem.*, 66:3744–3750 (1994).)

Several methods of capillary temperature control are presently employed, including forced air convective cooling and the use of liquid coolant. For example, U.S. Pat. No. 5,021,646 to Weinberger et al., hereby incorporated by reference, describes a capillary electrophoresis unit utilizing an air cooled cartridge. The temperature of the capillary is determined by measuring its electrical resistance. When the temperature of the capillary requires adjustment, a fan drives air cooled by a Peltier heat sink across the capillary in the cartridge. Similarly, U.S. Pat. No. 5,122,253 to Christianson, hereby incorporated by reference, describes the use of a stream of pressurized gas in a transverse flow through a capillary region. A rotary fan creates a gas flow which is axial to the helix formed by the capillary tube. This is intended to cool the capillary.

A liquid cooling apparatus is taught by U.S. Pat. No. 5,198,091 to Burolla et al., hereby incorporated by reference. The cooled capillary cartridge is bisectional and contains an inner chamber. The inner chamber holds the capillary and also can contain a circulating liquid coolant. The coolant is described as either water or, preferably, a completely fluorinated hydrocarbon. U.S. Pat. No. 5,164,064 to Dill et al., hereby incorporated by reference, reports an improved liquid cooled device. The device includes a capillary cartridge with a coolant flow channel. The coolant flow channel is advertised as having little or no dead volume to improve uniform cooling.

U.S. Pat. No. 5,183,101 to Penaluna et al., hereby incorporated by reference, combines a liquid cooled system with a refrigeration device. The device is comprised of a heat exchanger, a compressor and a capillary. The housing and electrical units of the refrigeration system are electrically insulated from the buffer solution, and the buffer solution is passed through the refrigeration coils to cool it as necessary. Alternatively, warm coolant from the compressor discharge can be directed to the heat exchanger for the warming of the electrode buffer as necessary.

All of the above-described approaches have shortcomings. For example, liquid cooling can be effective, but it is complicated. The capillary must be surrounded with a flowing, heat-conductive liquid; this presents concerns regarding leakage and electric shortages in the system. Forced air cooling is limited in its capacity to remove heat from the capillary column. This lack of an efficient system for removing heat from the capillary device limits the usefulness of capillary electrophoresis as a whole.

What is needed is a cooling means that will cool the capillary in an efficient manner to expand the usefulness of capillary electrophoresis.

SUMMARY OF THE INVENTION

The invention relates to electrophoresis and more particularly, to means for cooling capillary electrophoresis devices. The present invention exploits the advantages of a metal heat sink, with attention to electrical insulation of the buffer reservoirs from the heat sink for operation at higher voltages. Due to the increased effective cooling, the present invention also contemplates new, large capacity capillary tubes and capillary electrophoresis conducted in parallel arrays.

In one embodiment, the device comprises a capillary tube, a housing dimensioned to substantially enclose said tube, said housing comprising grooved electrically conductive material dimensioned to accept said tube.

In one embodiment, the device of the present invention comprises first and second radiator plates comprised of an electrically conductive material. While the present invention is not limited to the specific design of the plates, in one embodiment, the plates have an inner surface, at least one groove on the inner surface, outer surfaces and an insulative layer on at least one of the outer surfaces. A variety of electrically insulative material can be used for the outer surface in the present invention, including, but not limited to, ceramic, polymer and polyimide.

While numerous electrically conductive materials can be utilized, in one embodiment, the device is comprised of aluminum. However, other metals (e.g., copper) and alloys (e.g., brass) are contemplated.

In one embodiment, at least one of the outer surfaces of the radiator plates is finned. While a variety of fin dimensions are envisioned, preferably the fins are dimensioned at 1 inch by 3 inches by ⅛ inch.

It is not intended that the present invention be limited by the dimensions of the groove. However, in one embodiment, the groove is dimensioned such that at least half the outer circumference of a more than 400 micrometer cylindrical capillary tube can be accepted. Furthermore, the invention is not intended to be limited by the number of grooves; in one embodiment, there is more than one groove on the inner surface.

In one embodiment the device has an opening in the first or second or both radiator plates. In one embodiment, this opening intersects the groove. This opening facilitates optical measurements.

Furthermore, it is contemplated that in one embodiment, a second electrically insulative layer can be place in the groove. This layer may be comprised of a variety of materials, including, but not limited to a polymer (e.g., polyimide).

In one embodiment, the method for performing electrophoresis comprises a) providing: i) the device as described above ii) first and second buffer reservoirs; iii) a capillary electrophoresis tube having first and second ends in fluidic communication with said first and second buffer reservoirs; and iv) an electrical source connected to said first and said second buffer reservoirs; and b) placing said tube between said first and second radiator plates; and c) introducing electric current to said first and second buffer reservoirs with said electric source. Due to the effective cooling of the present invention, in another embodiment the voltage of the electric current is greater than 30 kV.

In one embodiment, the method further comprises introducing, prior to step c), a sample into said first end of said tube. In another embodiment, the method further comprises viewing said tube through the opening to observe movement of a sample.

In yet another embodiment the method, further comprises a forced air means and passing forced air over said first and second radiator plates with said forced air means. While not intended to limit the scope of the present invention, the force air means can be a fan or a pressurized air tank.

Due to the efficient cooling of the present invention, new, large capacity capillary tubes are encompassed by the present invention. In one embodiment, the tube has an inner diameter greater than 400 micrometers. In another embodiment, this tube is cylindrical. Alternatively, the tube has a polygonic cross-section; and in another embodiment, has cross-section dimensions between one hundred micrometers by four hundred micrometers and one hundred micrometers by one centimeter.

The tube can be composed of numerous materials, including, but not limited to, teflon, glass, quartz, ceramic, plastic, rubber and polyurethane. Additionally, in one embodiment, tube can be coated with any number of insulative materials, including, but not limited to a polymer (e.g., polyimide).

In one embodiment, the method encompasses the use of multiple electrophoresis tubes (e.g., between 2 and 32 and more preferably between 32 and 96) utilizing the same buffers and electric source. Due to the effective cooling of the present invention, more than 96 tubes may be utilized in parallel array for sequencing and other purposes.

Electric field: A, 100 V/cm; B, 250 V/cm; C, 500 V/cm; D, 750 V/cm; E, 1000 V/cm; F, 1250 V/cm; G, 1500 V/cm; H, 1750 V/cm.

Figure 4:
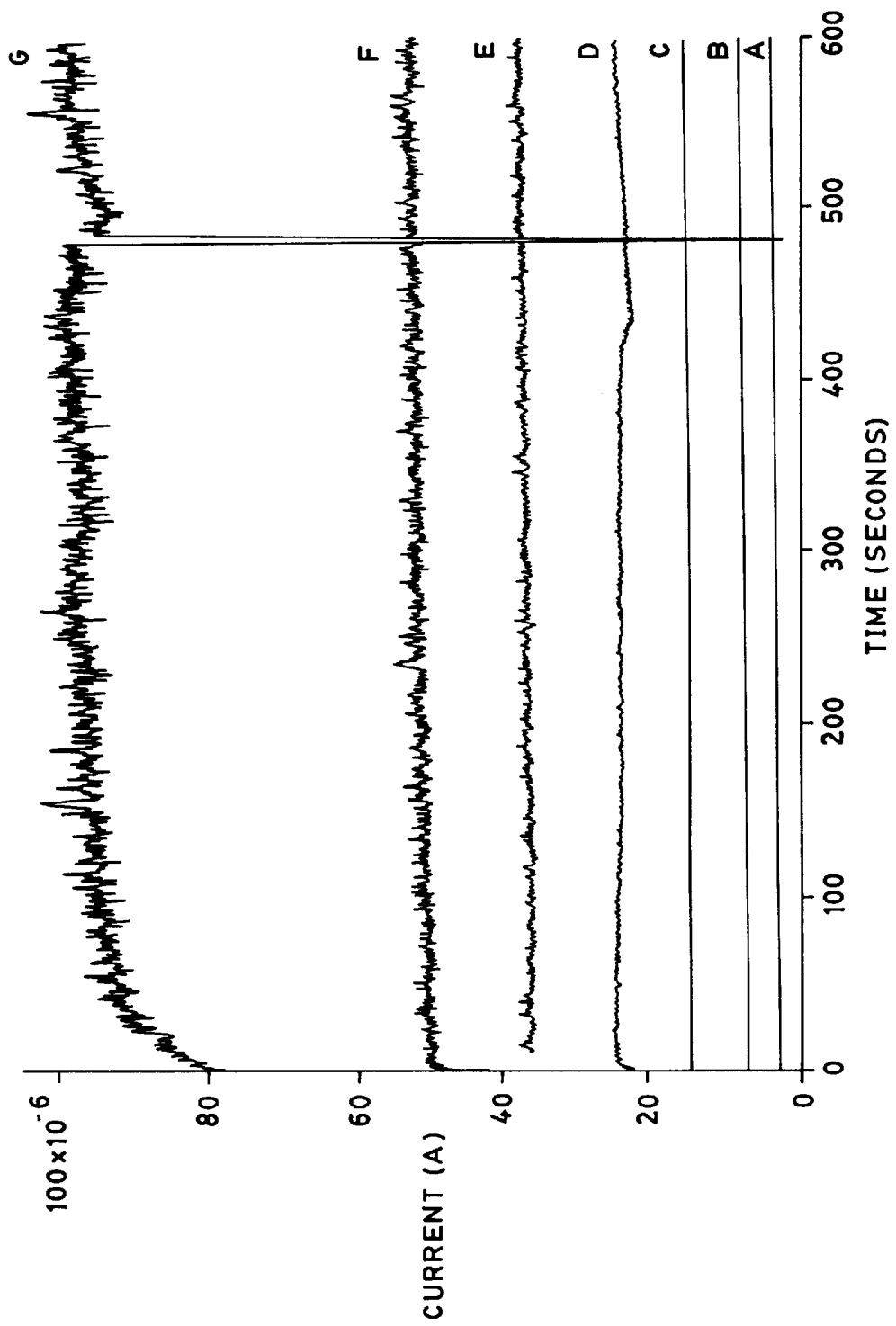

FIG. 4 is a diagram of the time dependence of current in a 75 micrometer (inner diameter) fused silica capillary containing 1×TBE and cooled by forced air convection only. Electric field: A, 100 V/cm; B, 250 V/cm; C, 500 V/cm; D, 750 V/cm; E, 1000 V/cm; F, 1250 V/cm; G, 1500 V/cm.

Figure 5A:
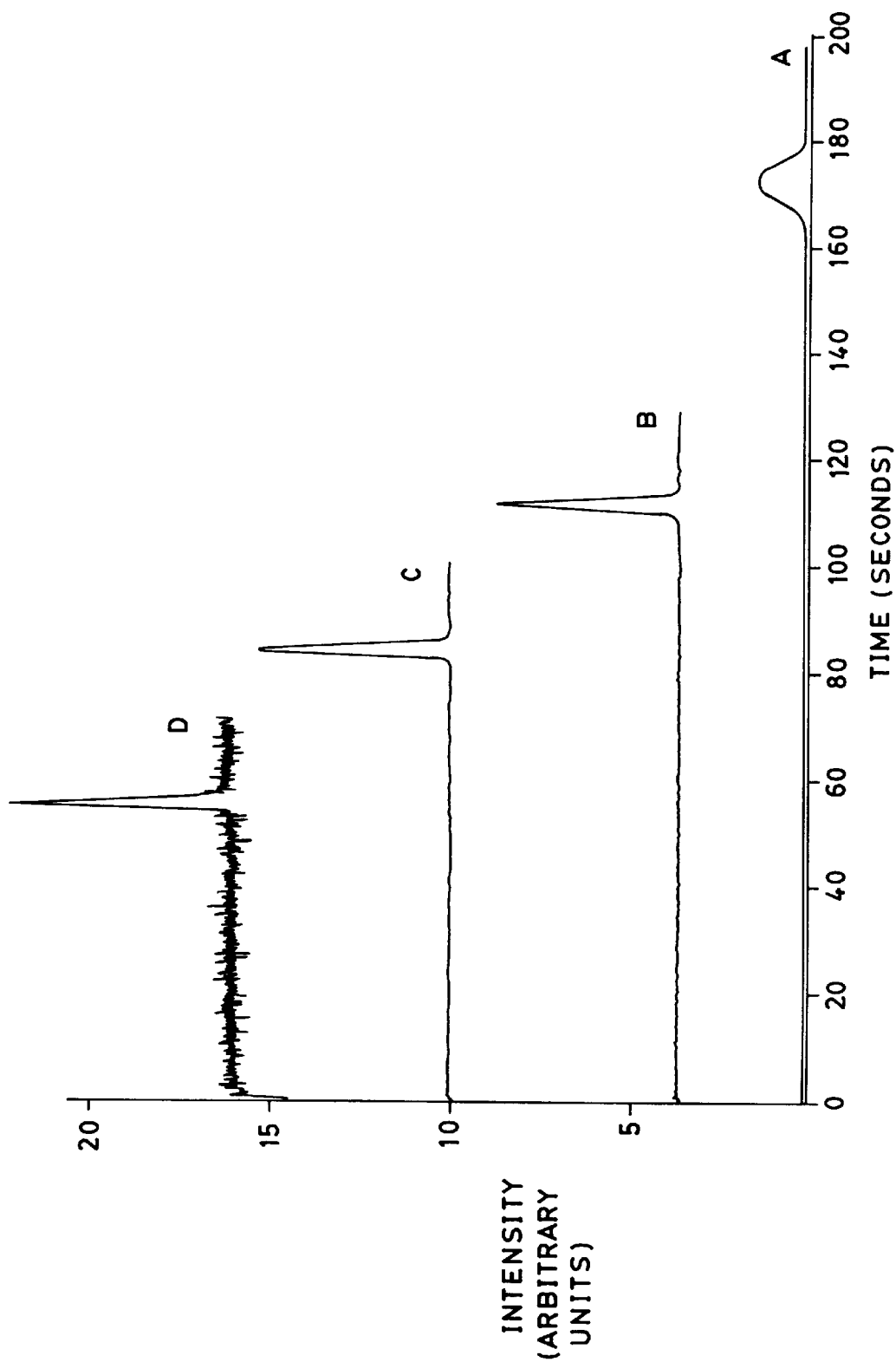
Figure 5B:
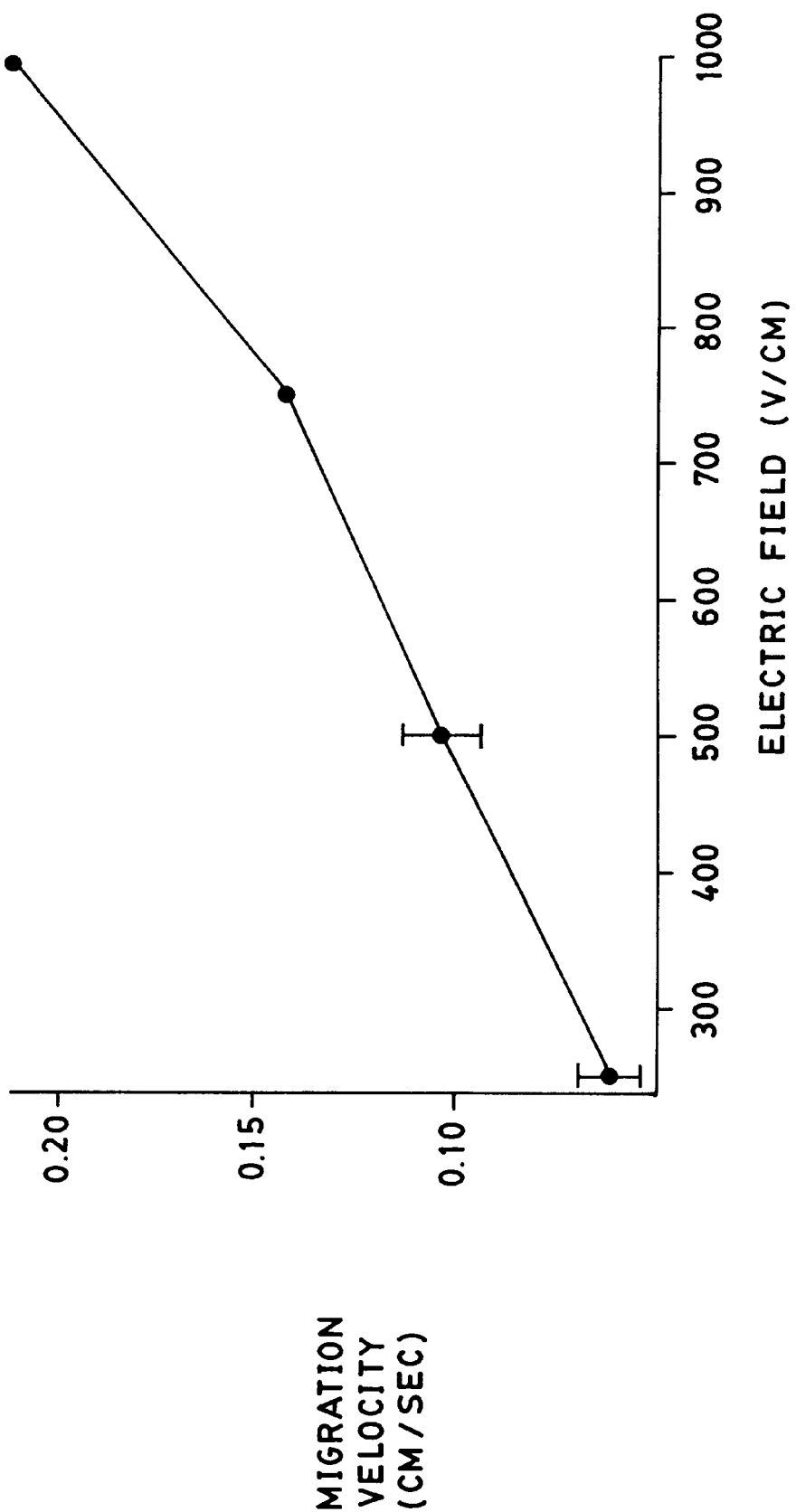

FIG. 5 is an electropherogram of erythrosin B (an illustrative sample peptide) in 1×TBE, 75 micrometer inner diameter capillary, cooled by an aluminum embodiment of the heat sink of the present invention with forced air convection. Electric field: A, 250 V/cm; B, 500 V/cm; C, 750 V/cm; D, 1000 V/cm. Inset plot is the average migration velocity of erythrosin B versus applied electric field.

DEFINITIONS

As used herein, the term "radiator plates" means a block of material that conducts heat. The present invention is not limited by the construction of the plate. For example, the present invention contemplates single cast blocks, as well as half-plates that are assembled in a "sandwich" mode (relative to the tube).

As used herein, the term "inner surface" means a side of a radiator plate dimensioned such that, when placed in contact with a second radiator plate, the surfaces of the two radiator plates are substantially connected.

As used herein, the term "outer surface" refers to a side of a radiator plate other than the inner surface.

As used herein, the term "electrically conductive material" means a material that conducts an electric current more efficiently than air (e.g., a metal).

As used herein, the term "electrically insulative material" means a material that conducts an electric current less efficiently than air (e.g., ceramic or polyimide).

As used herein, the term "finned" refers to having raised structures or indentations interspaced on a surface, increasing its overall surface area (e.g., bumps, lines, gouges, etc).

GENERAL DESCRIPTION OF THE INVENTION

The invention relates to electrophoresis and more particularly, to means for cooling capillary electrophoresis devices. The present invention contemplates a system wherein the capillary is pressed between electrically conductive (such as metal) blocks which dissipate heat. In one embodiment, the blocks are finned on their outer surfaces for increased surface area. While the present invention contemplates a variety of materials, aluminum is chosen in this description as it is lightweight, is easy to machine and is an excellent heat conductor.

There are two insulation issues when operating the capillary electrophoresis cooling means of the present invention: a) electric insulation between the capillary tube and the heat sink and b) electric insulation between the heat sink and the electrophoretic buffers. When working with standard, commercially available electrophoresis capillary tubes, this device exploits the high dielectric strength of the capillary polyimide coating (1575 kV/cm) (see *Flexible Fused Silica Capillary Tubing Standard Product List*, Polymicro Technologies, Inc., Phoenix, Ariz., (1996)). When working with nonstandard, large diameter tubes enabled by the present invention, insulation must be provided on the capillary tube or within the heat sink itself. Such insulation may be of a variety of materials, including the polyimide coating described above. Additionally, the metal is insulated from the buffer reservoirs by an insulative layer. A number of materials may comprise this layer, including ceramic and polymer.

In one embodiment, the method contemplates providing two radiator plates (each comprised of an electrically conductive material) two buffer reservoirs, a capillary electrophoresis tube, an electrically insulative material, a sample, and an electrical source. The tube is placed between the radiator plates with the sample on one end of the tube. One end of the tube is placed in contact with the first buffer reservoir, and the other end of the tube is placed in the second buffer reservoir. The insulative layer is situated between the buffer reservoirs and the radiator plates. Subsequently, electric current is introduced to the buffer reservoirs.

The charge on the inner capillary wall, q, depends upon the applied voltage, the dielectric constant of the material, and the geometry of the capillary, as given in the following equation (see F. W. Peek et al. *Dielectric Phenomena in High Voltage Engineering, Second Edition*; McGraw-Hill Book Co., Inc.: New York, N.Y., 1920:

$$q = CV = (kA\epsilon_o/x)V = [kA(10^9/4\pi c^2)/x]V$$

where C is capacitance (Farads), $\epsilon_o$ is the absolute permittivity of air (Farads/cm), k is the dielectric constant or relative permittivity (i.e., k=1 for air), x is the length of the capillary (cm), $A=2\pi rx$ is the surface area (cm$^2$), c is the velocity of light (cm/sec), r is the radial distance from the center of a cylinder (cm) and V is the applied potential difference (volts). The following equation describes the displacement field, D (V/cm). At any point D is directly proportional to the charge and thus the electric field, E (V/cm) (see Peek, supra):

$$D = CV/A = (dV/dr)k\epsilon_o = Ek\epsilon_o$$

The breakdown voltage of a capillary can be derived with the following assumptions. The system is modeled as a cylindrical capacitor with three dielectric materials in series (see Peek, supra). The aluminum heat sink is modeled as a perfect conductor and ground is infinitely far away. In order to satisfy the first assumption, the total capacitance of the system is calculated as an infinite series of capacitors with boundary conditions:

$$\frac{1}{C_T} = \int d\left(\frac{1}{C}\right) = \frac{2c^2}{k_1 10^9} \int_{r=R_0}^{r=R_1} \frac{dr}{r} + \frac{2c^2}{k_2 10^9} \int_{r=R_1}^{r=R_1} \frac{dr}{r} + \frac{2c^2}{k_3 10^9} \int_{r=R_2}^{r=\infty} \frac{dr}{r}$$

The conversion factor, $10^9$, is required to keep the units of capacitance in Farads. The total capacitance is used to approximate the breakdown voltage of a fused silica, polyimide coated capillary can be calculated (see T. L. Rapp, *Temperature Control in Capillary Electrophoresis*, Thesis, University of Michigan, Ann Arbor, Mich., 1996, Appendix):

$$V_{max} = Krk_r\left[\frac{1}{k_1}\ln(R_1/R_0) + \frac{1}{k_2}\ln(R_2/R_1) - \frac{1}{k_3}\ln(R_2)\right]$$

In this equation, $k_1$, $k_2$, and $k_3$ are the dielectric constants of fused silica, polyimide and ir, respectively. $R_o$, $R_1$ and $R_2$ are the internal radius of the capillary, the outer radius of the fused silica and the outer radius of the capillary, respectively.

The first, second and third terms contained in brackets in the above equation represent the resistance to dielectric breakdown contributed by the fused silica, polyimide and air, respectively. Electrical insulation breaks down at any point where the displacement field exceeds the dielectric strength of the strongest material (see Peek supra). Since the displacement field is greatest along the surface of the conductor, the appropriate value of r is the outer radius of the conductor. The appropriate values of K and $k_r$ are the dielectric strength and constant of the material in contact with the outer surface of the conductor.

While the present invention is not limited by the geometry of the fins, a rectangular shape is assumed for the fins on the aluminum blocks containing the capillary. The heat transport of a rectangular fin is (see T. L. Rapp, *Temperature Control in Capillary Electrophoresis*, Thesis, University of Michigan, Ann Arbor, Mich., 1996, Appendix; and J. P. Holman, *Heat Transfer, Sixth Edition*; McGraw-Hill Book Company, 1986:

$$q = \sqrt{hPkA}\,(T_o - T\infty)\frac{\sinh(mL) + (h/mk)\cosh(mL)}{\cosh(mL) + (h/mk)\sinh(mL)}$$

where q is the heat dissipated by each fin (W), h is the convective heat transfer coefficient (W/m$^{2\cdot °}$ C.), k is thermal conductivity (W/m$^{2\cdot °}$ C.), m=√hP/kA is the temperature of the wall at the base of the fin (° C.), and T∞ represents the ambient temperature (° C.). A is the cross-sectional area of the fin (m$^2$), L is the height of the fin (m) above the heat sink, t is the fin width (m), Z is the length of the fin (m), and P=2t+2Z is the perimeter of the end of the fin.

The assumptions made in the derivation of this equation are that the fin is of finite length and that it loses heat by convection from its end. This shows that the greater the fin length and the thinner the fin, the better the heat dissipation.

DESCRIPTION OF THE PREFERRED EMBODIMENTS

Standard CE tubes, as described above, have an inner diameter of 4 to 400 micrometers. This small cross-section of analytical capillaries limits their use in preparative electrophoresis. Due to the efficient cooling of the heat sink contemplated by the present invention, new, larger cross-section capillary electrophoresis tubes are envisioned. While a variety of tube shapes are contemplated, because the heat transport of a capillary tube is governed its cross-sectional dimension, especially good heat transport can be obtained in such large-capacity capillaries with the use of rectangular cross-section tubes. In one embodiment, the new capillary tubes have cross-sectional dimensions exceeding 100 micrometers by one centimeter.

Given the benefits and teachings of the present invention, one of skill in the art is capable of manufacturing these tubes from a variety of materials, including glass, ceramic, plastic material, rubber, polyurethane, teflon, quartz, etc. See U.S. Pat. No. 3,620,958 to Dijksterhuis el al., hereby incorporated by reference.

As a further consequence of the excellent cooling effects of the present invention, multiple electrophoresis capillaries can be placed in parallel arrays. This simultaneous use of many capillaries in a parallel array increases the overall throughput of electrophoresis. Multiple capillaries are analogous to multiple lanes in standard gel electrophoresis. In this example, multiple grooves are milled in the interior surface of the metal heat sink to accommodate each capillary tube. The tubes are loaded individually, but run in the same anode and cathode buffers and utilize a single power supply.

It is not intended that the invention be limited by the precise number of capillaries. Nonetheless, as a consequence of its cooling effectiveness, the present invention can cool more than 96 capillaries operating in parallel array.

EXPERIMENTAL

The following examples serve to illustrate certain preferred embodiments and aspects of the present invention and are not to be construed as limiting the scope thereof.

In the experimental disclosure which follows, the following abbreviations apply: ° C. (Centigrade); Am (micrometers); mm (millimeters); cm (centimeters); DC (direct current); mW (milliwatts); kV (kilovolts).

EXAMPLE 1

Heat Sink Construction

While the present invention contemplates a variety of radiator shapes, in this example, the radiator is constructed of two finned aluminum blocks with two quarter-inch MACOR machinable ceramic (Corning Glass Works, Inc., Corning, N.Y.) blocks on the lower surfaces to prevent arcing to the buffer reservoir electrodes. The fins are 1"×3"× ⅛" set ⅛" apart.

Figure 1:
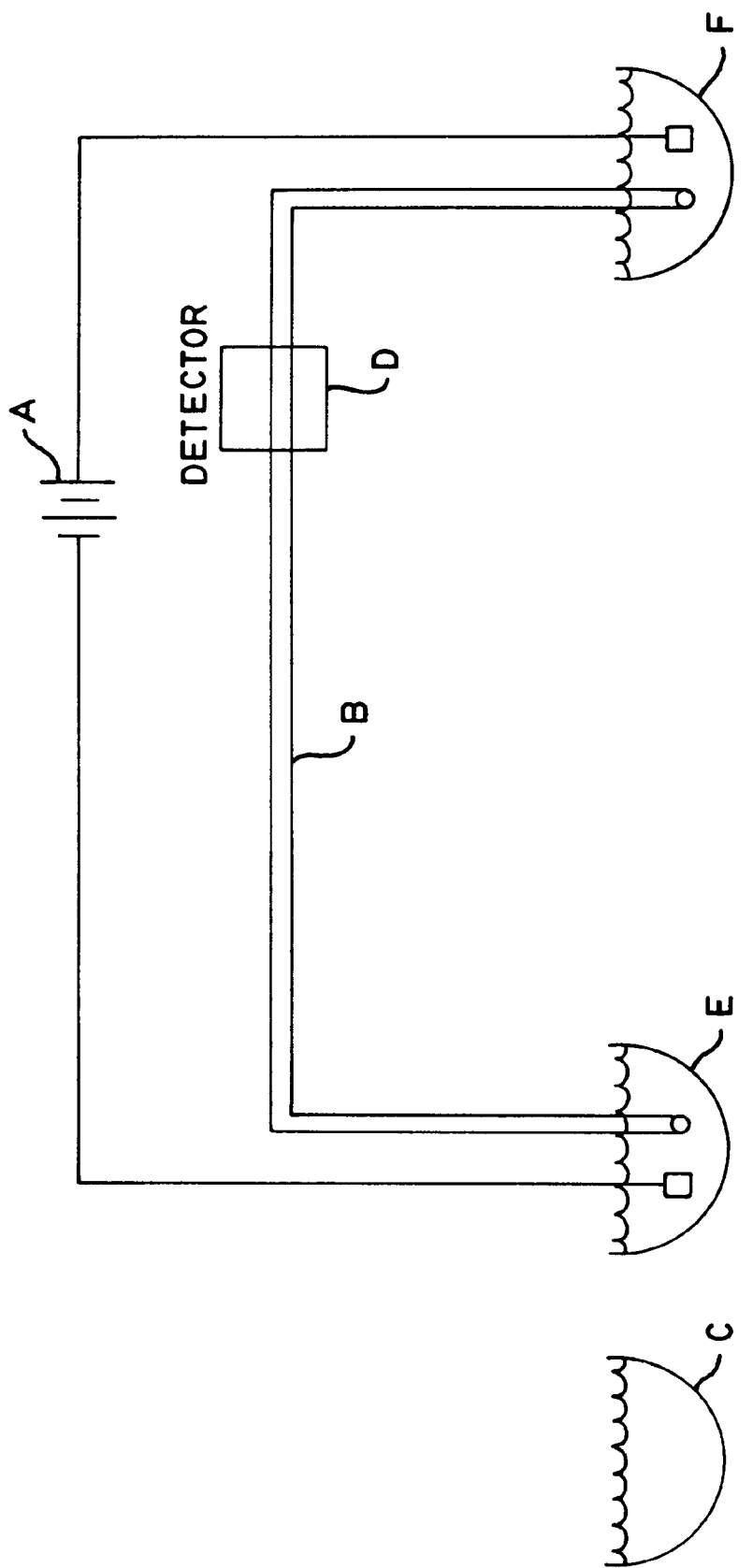
FIG. 1 schematically depicts a typical CE apparatus. A high intensity electrical field supplied by high voltage power supply A is applied across a separation capillary tube B of narrow inside diameter (e.g., approximately 5 to 400 micrometers) containing an electrolytic buffer solution. For an uncoated, open capillary tube, the presence of the electrical field imparts motion to charged and uncharged moieties present in the buffer through two mechanisms: electro-osmotic (endo-osmotic) flow and electrophoretic force. Flow of buffer (or sample from sample reservoir C) through capillary B is detected by a detector D. Electro-osmotic flow is the bulk flow of buffer from a first buffer reservoir E to a second buffer reservoir F through capillary B due to the shearing movement of a diffuse layer of cations past a more firmly held, dense layer, interacting with integral, anionic groups of the capillary wall.
Figure 2A:
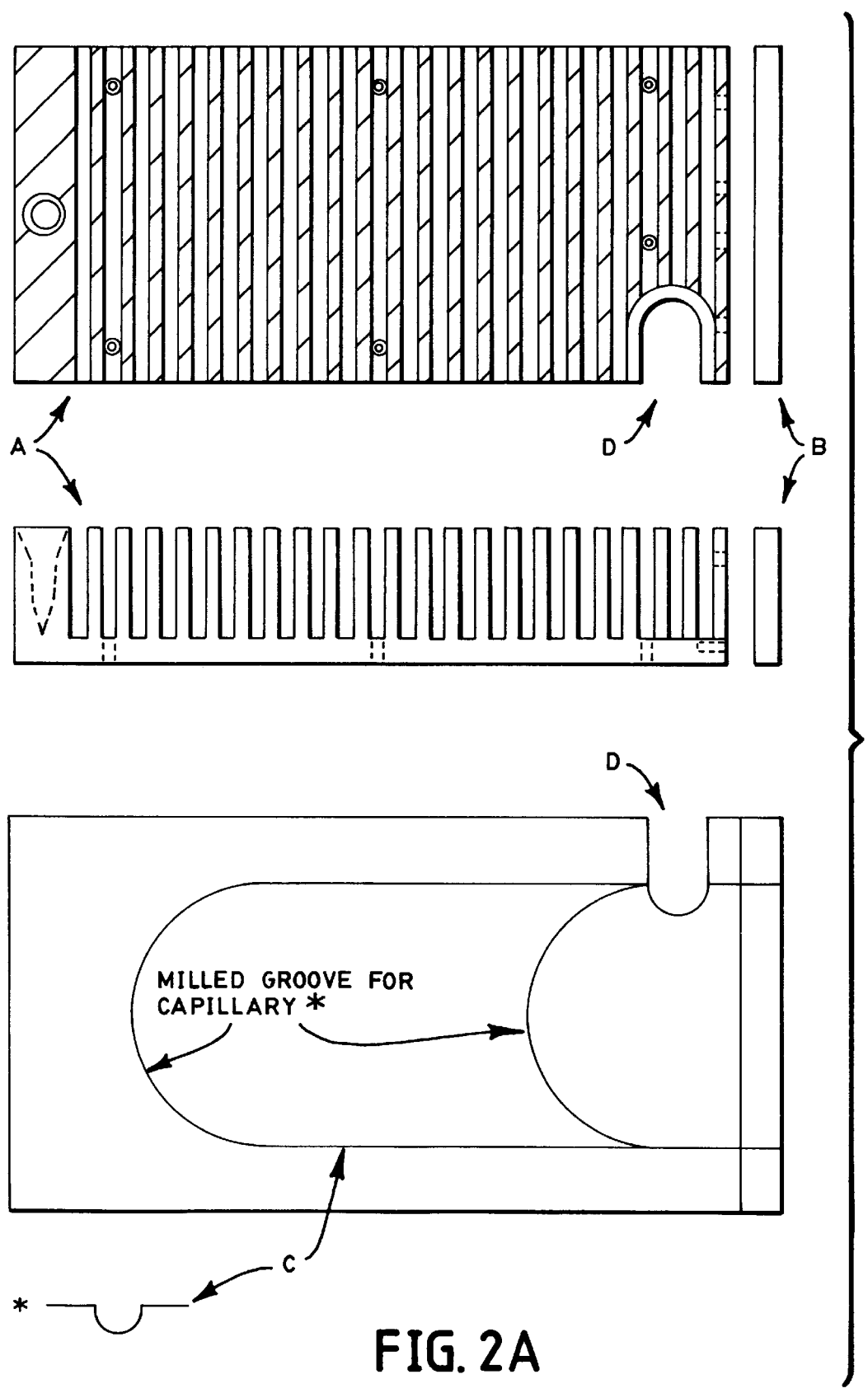
FIG. 2A is a diagram of the basic configuration of the exterior and interior of one embodiment of the cooling means of the present invention. The fins, A, of the heat sink are spaced to permit effective cooling, while the insulator, B, protects the fins from the electric current. The interior surface of the heat sink has milled grooves, C, for capillaries (* shows the grooves in cross-section). An opening, D, is provided to allow for the viewing of sample migration in the tube. The opening, D, is designed such that it intersects the milled groove, C, in a manner that a portion of a capillary tube in the device will be conveniently exposed for sample detection.

The heat sink is illustrated in FIG. 2A. This design accommodates 15 and 30 centimeter length capillaries. A one centimeter opening is milled in the cooling block for optical detection. The grooves milled in the aluminum blocks have U-shaped cross-sections to provide maximum thermal contact to the capillary.

Forced air cooling is provided by a 4" equipment cooling fan, circulating 0.05 m$^3$/sec. The same fan is used for forced air cooling of unenclosed capillaries.

Practical fin dimensions are governed by several factors. While various parameters are contemplated, in this example, length and spacing of the fins was chosen to be adequate to allow dissipation of approximately 5 Watts with forced air convection using a fan which circulates air at 0.05 m$^3$/s. Preferably, in order to provide sufficient space for air flow around the fins, the space between the fins should not be smaller than the width of the fins. Removing a large fraction of material from a metal block causes the internal stresses to warp the remaining material. Preferably, the two halves of the cooling block should fit smoothly together to provide complete thermal contact with each other and the capillary contained between them. Thus, a compromise was made between heat dissipation and structural integrity of the cooling block. The thermal and electrical data for the materials used to construct the heat sink are shown in Table 1. The present model accommodates 15–30 cm length capillaries. If longer capillaries are required, serpentine capillary pathways could be easily milled into the heat sinks.

EXAMPLE 2

Electrophoresis Apparatus

The present invention contemplates that the heat sink can be employed with commercially available conventional CE, as well as CE enabled by the heat dissipation capabilities of the disclosed heat sink. In this example, the CE apparatus was conventional. Briefly, it consisted of a DC power supply and buffer reservoirs. The electrophoresis current was monitored with the internal circuit of the power supply and digitized (10 samples/sec) by a Metrabyte DAS-16 ADC board (Keithley Metrabyte, Taunton, Mass.) in an IBM compatible 80386-microprocessor based computer. Fluorescence was excited by a 2.5 mW green He-Ne laser (Melles Griot, Irvine, Calif.). The fluorescence emission was passed through two orange cut-off filters (Melles Griot, Irvine, Calif.) and collected by a photomultiplier tube (Hamameters Corp., Bridgewater, N.J.). The entire high voltage electrophoresis system was enclosed in a locally-constructed Plexiglas safety box. A Fisher Scientific digital conductivity meter (Model 09-326-2) (Fisher Scientific, Pittsburgh, Pa.) and a Precision water bath used to make the bulk conductivity measurements of the test solutions.

A: Capillary Preparation

For the current measurements, all capillaries were 15±0.1 cm in length. The fused silica, polyimide coated capillaries (Polymicro Technologies, Phoenix, Ariz.), were 75 micrometer inner diameter, 365 micrometer outer diameter. No window was burned in the polyimide coating. For fluorescence detection, an observation window of 8–10 mm long was burned through the polyimide coating approximately 3 cm from the exit end of the capillary. All capillaries were conditioned by passing successively 1 M HCl, 1 M NaOH, deionized/filtered $H_2O$, and 1×TBE through them for 2 minutes each.

B: Solution Preparation

The fluorophore used to test the apparatus was $1\times 10^{-4}$ M erythrosin B (Molecular Probes, Inc., Eugene, Oreg.) in 1×TBE buffer (90 mM tris base, 90 mM boric acid and 20 mM ethylenediamine tetraacetic acid, all American Chemical Society reagent grade). The pH of this solution was ca. 8.3. All solutions were prepared with deionized water which was filtered twice through 0.22 micrometer membrane filters (Millipore corp., Bedford, Mass.). The completed solutions were filtered again through 0.22 micrometer membrane filters before use.

C: Conductivity Measurements

The temperature dependence of the conductivity of 1×TBE was measured with a thermocouple (Omega Engineering, Stamford, Conn.) over the range of 21°–56° C. Conductivity was used to measure the average internal temperature of operating capillaries.

D: Capillary Breakdown Calculations and Observations

In the concentric dielectric model of the capillary when dielectric breakdown of a layer occurs, the material essentially becomes a conductor. System insulation is therefore governed by the material with the highest breakdown voltage.

The equations above predict that the capillary can withstand 15.4–24.6 kV before breakdown of the fused silica occurs. The range in breakdown potential is a result of the range in the dielectric strength reported for fused silica. With silica breakdown, the polyimide and air are the only dielectric materials. The fused silica term in the equation disappears, r is set equal to $H_1$, and K is set equal to the dielectric strength of polyimide. Thus, the polyimide should withstand a maximum of 361.6 kV before dielectric breakdown occurs.

Although remarkably high breakdown voltages might be predicted, it was found that only 26–31 kV could be applied across a capillary before arcing occurred. There are two possible pathways for relatively low voltage arcing. A pathway is directly from the high voltage electrode in the buffer reservoir, through air to the aluminum holder and through air again to the ground electrode. Arcing can also occur through vapor bubbles formed inside the short section of capillary between the heat sink and the high voltage buffer reservoir. Therefore the voltage at which arcing occurred depended upon the quality of the electrode and buffer reservoir electrical insulation and also the length of the capillary outside the aluminum heat sink/radiator. No evidence of arcing through the capillary walls, such as distortion or discoloration of the polyimide coating, was observed. These observations suggest that the basic design of the heat sink is sound.

We observed that if a capillary was reused after arcing had occurred, subsequent internal arcing would occur at lower voltages. When glass breakdown occurs many cracks form throughout the material (see Peek supra). These cracks can cause nonuniformities in the local electric field and greater opportunities for hot spot formation.

EXAMPLE 3

Heat Sink Performance

Figure 2B:
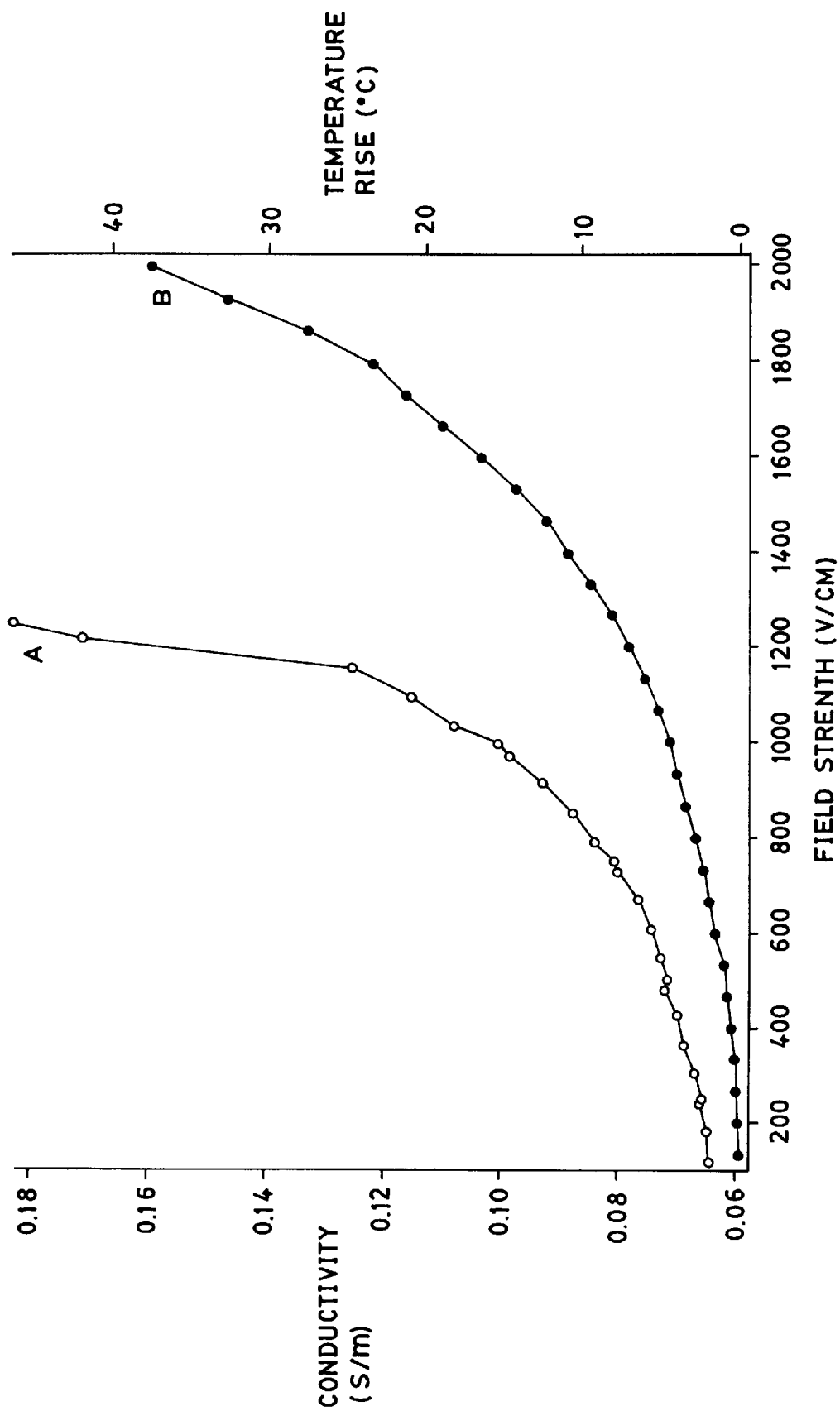
FIG. 2B is a diagram demonstrating the conductivity of buffer (e.g., 1×TBE) as a function of electric field in a 75 micrometer (inner diameter) fused silica capillary cooled by forced air convection only, A, and the heat sink of the present invention, B. The calculated temperature rise is shown on the right vertical axis.

The performance of the aluminum heat sink and radiator is compared with the performance of forced air cooling of an unenclosed capillary in FIG. 2. Both the conductivity and derived temperature changes in 1×TBE (bulk conductivity, 0.0890–0.0915 S/m at 21° C., 0.00263 S/m/° C.) are shown. The heat sink can limit the internal temperature rise to less than 5° C. above ambient at 1000 V/cm and less than 10° C. above ambient at 1300 V/cm. Forced air cooling of an unenclosed capillary can only limit the internal temperature rise to less than 10° C. above ambient at 800 V/cm.

Figure 3:
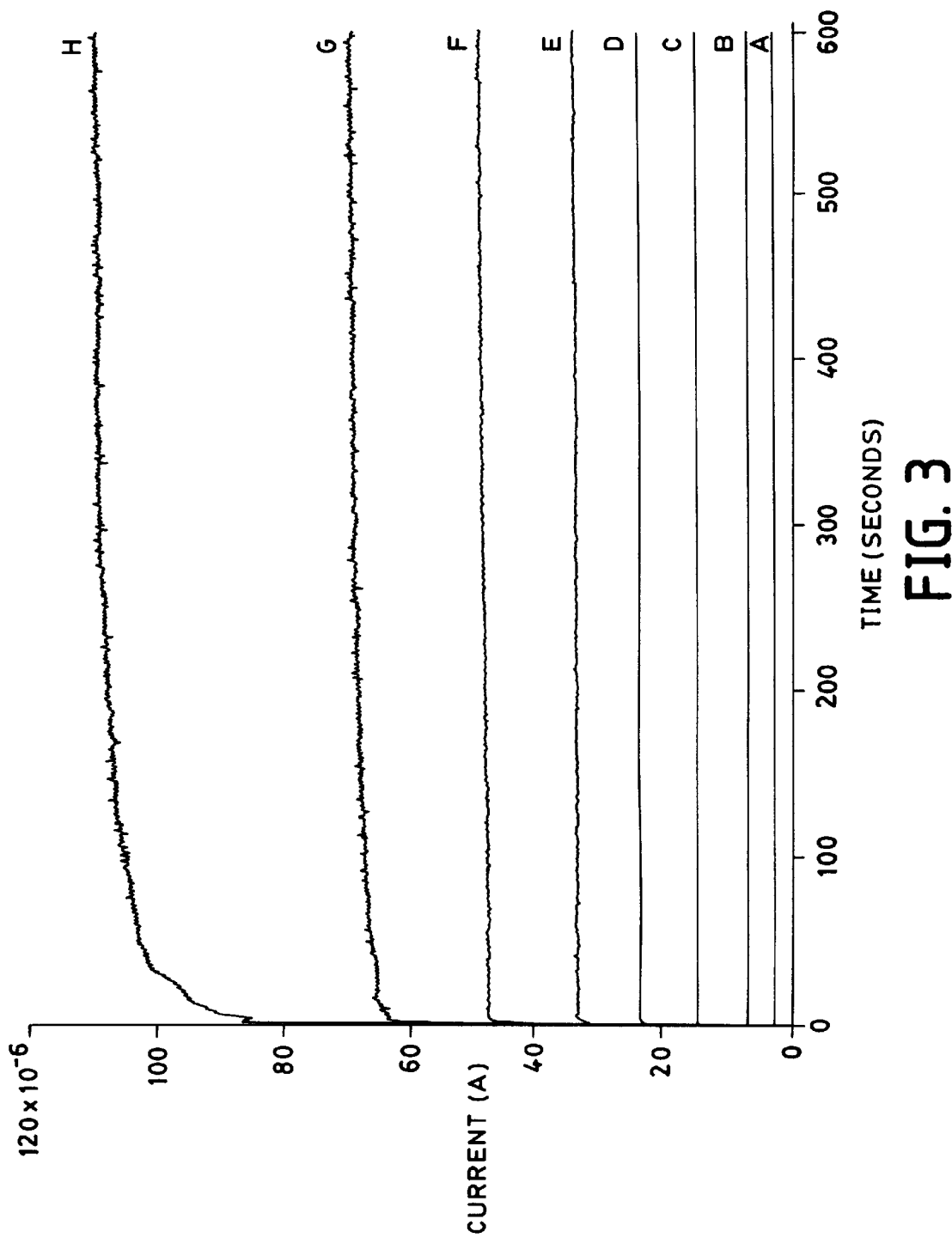
FIG. 3 is a diagram of the time dependence of current in a 75 micrometer (inner diameter) fused silica capillary containing 1×TBE and cooled in an aluminum embodiment of the heat sink of the present invention with forced air convection.

The time dependence of internal current was monitored at several electric fields (FIG. 3). After a short rise time, the aluminum heat sink/radiator provides a constant steady state temperature up to 1500 V/cm. At 1750 V/cm heat dissipation was inadequate to allow attainment of steady state. During the last 450 seconds, the temperature rises about 3.5° C.

FIG. 4 shows the performance of forced air cooling of an unenclosed capillary system. The current fluctuations are large, but this system can provide a constant temperature environment, after a brief rise time, up to 1250 V/cm. Above that electric field, its performance deteriorates rapidly. Unsteady current (temperature) is observed at 1500 V/cm. In the run illustrated in the figure, the increased temperature and consequent outgassing causes bubble formation. A bubble is the source of the current spike in data line G.

FIG. 5 shows erythrosin B migration through the capillary at electric fields ranging from 250–1000 V/cm. The slope of the average migration velocity versus electric field plot is almost constant up to 1000 V/cm which is consistent with a constant internal capillary temperature close to ambient, about 22° C.

From the above, it should be clear that the present invention provides a cooling means that is a simple, cost-effective temperature control system for capillary electrophoresis. In the aluminum heat sink embodiment with a nonelectroconductive layer between the metal radiator and the electrophoresis buffer protects against overheating and electric arcing between the buffer and the heat sink. The cooling means easily outperforms conventional forced air cooling and compares favorably with circulating liquid systems.

We claim:

1. A method for performing electrophoresis, comprising:
   a) providing:
      i) first and second radiator plates comprised of a metal selected from the group consisting of aluminum, copper and brass, having inner surfaces, outer surfaces and a first electrically insulative material on at least one of said outer surfaces, said inner surface of said first radiator plate comprising at least one groove dimensioned to accommodate a tube, wherein said groove is coated with a second electrically insulative material, said insulative material comprising polyimide;
      ii) first and second buffer reservoirs;
      iii) at least one capillary electrophoresis tube having first and second ends in fluidic communication with said first and second buffer reservoirs; and
      iv) an electrical source connected to said first and said second buffer reservoirs; and
   b) placing said tube in complete thermal contact with said first and second radiator plates such that said tube is approximated with the inner surfaces of said first and second plates;
   c) introducing electric current to said first and second buffer reservoirs with said electric source under conditions that the operating voltage of said electric current is greater than 30 kV.

2. The method of claim 1, wherein at least one of said outer surfaces of said first and second radiator plates is finned.

3. The method of claim 2, wherein said fins are dimensioned at 1 inch by 3 inches by ⅛ inch.

4. The method of claim 1, wherein said plates have an opening positioned to intersect said grooves.

5. The method of claim 4, further providing a step before step c), of introducing a sample to said first end of said tube, and after step c), step d) viewing said tube through said opening to observe movement of said sample.

6. The method of claim 1, further comprising the step of passing forced air over said first and second radiator plates.

7. A method for performing electrophoresis, comprising:
   a) providing:
      i) first and second radiator plates comprised of a metal selected from the group consisting of aluminum, copper and brass, having inner surfaces, outer surfaces and a first electrically insulative material on at least one of said outer surfaces, said inner surface of said first radiation plate comprising at least one groove dimensioned to accommodate a tube, wherein said groove is coated with a second electrically insulative material, said insulative material comprising polyimide, wherein said radiator plates incorporate a plurality of fins;
      ii) first and second buffer reservoirs;
      iii) at least one capillary electrophoresis tube having first and second ends in fluidic communication with said first and second buffer reservoirs; and
      iv) an electrical source connected to said first and said second buffer reservoirs; and
   b) placing said tube in complete thermal contact with said first and second radiator plates such that said tube is approximated with the inner surfaces of said first and second plate;
   c) introducing electric current to said first and second buffer reservoirs with said electric source under conditions that the operating voltage of said electric current is greater than 30 kV.

8. The method of claim 7, further comprising the step of passing forced air over said first and second radiator plates.

9. The method of claim 7, further providing a step before step c), of introducing a sample to said first end of said tube, and after step c), step d) viewing said tube through said opening to observe movement of said sample.

10. A method for performing electrophoresis, comprising:
    a) providing:
       i) first and second radiator plates, said plates comprised of a metal selected from the group consisting of aluminum, copper and brass having inner surfaces, outer surfaces, said inner surface of said first radiation plate comprising at least one groove dimensioned to accommodate a tube, wherein said groove is coated with a polymer comprising polyimide and an electrically insulative material on at least one of said outer surfaces;
       ii) first and second buffer reservoirs;
       iii) at least one capillary electrophoresis tube having first and second ends in fluidic communication with said first and second buffer reservoirs; and
       iv) an electrical source connected to said first and said second buffer reservoirs; and
    b) placing said tube in complete thermal contact with said first and second radiator plates such that said tube is approximated with the inner surfaces of said first and second plates;
    c) introducing electric current to said first and second buffer reservoirs with said electric source, wherein the operating voltage of said electric current is greater than 30 kV.

11. The method of claim 10, further providing a step before step c), of introducing a sample to said first end of said tube, and after step c), step d) viewing said tube through said opening to observe movement of said sample.

12. The method of claim 10, further comprising the step of passing forced air over said first and second radiator plates.

* * * * *